United States Patent
Foley et al.

(10) Patent No.: US 6,676,665 B2
(45) Date of Patent: Jan. 13, 2004

(54) SURGICAL INSTRUMENTATION AND METHOD FOR TREATMENT OF THE SPINE

(75) Inventors: Kevin T. Foley, Germantown, TN (US); Jeff R. Justis, Gulf Breeze, FL (US)

(73) Assignee: SDGI Holdings, Inc., Wilmington, DE (US)

( * ) Notice: Subject to any disclaimer, the term of this patent is extended or adjusted under 35 U.S.C. 154(b) by 168 days.

(21) Appl. No.: 09/928,949

(22) Filed: Aug. 13, 2001

(65) Prior Publication Data

US 2002/0026197 A1 Feb. 28, 2002

Related U.S. Application Data

(60) Provisional application No. 60/224,491, filed on Aug. 11, 2000.

(51) Int. Cl.⁷ .................................................. A61B 17/66
(52) U.S. Cl. ....................................... 606/105; 600/201
(58) Field of Search .............................. 606/53, 76, 78, 606/86, 105, 191, 198; 600/201, 210, 235

(56) References Cited

U.S. PATENT DOCUMENTS

| | | | |
|---|---|---|---|
| 817,973 A | * 4/1906 | Hausmann | .................. 600/224 |
| 4,204,531 A | 5/1980 | Aginsky | |
| 4,854,312 A | 8/1989 | Raftopoulos et al. | |
| 4,995,868 A | 2/1991 | Brazier | |
| 5,059,193 A | 10/1991 | Kuslich | |
| 5,074,871 A | * 12/1991 | Groshong | .................. 606/170 |
| 5,108,404 A | * 4/1992 | Scholten et al. | .............. 606/94 |
| 5,171,278 A | 12/1992 | Pisharodi | |
| 5,390,683 A | 2/1995 | Pisharodi | |
| 5,423,850 A | 6/1995 | Berger | |
| 5,480,400 A | 1/1996 | Berger | |
| 5,554,101 A | * 9/1996 | Matula et al. | .............. 600/214 |
| 5,637,097 A | 6/1997 | Yoon | |
| 5,685,826 A | 11/1997 | Bonutti | |
| 5,690,606 A | 11/1997 | Slotman | |
| 5,693,100 A | 12/1997 | Pisharodi | |
| 5,707,390 A | 1/1998 | Bonutti | |
| 5,755,732 A | 5/1998 | Green et al. | |
| 5,782,713 A | 7/1998 | Yang | |
| 5,782,747 A | 7/1998 | Zimmon | |
| 5,785,647 A | 7/1998 | Tompkins et al. | |
| 5,827,289 A | 10/1998 | Reiley et al. | |
| 5,865,802 A | 2/1999 | Yoon et al. | |
| 5,882,340 A | 3/1999 | Yoon | |
| 5,972,015 A | 10/1999 | Scribner et al. | |
| 6,039,761 A | 3/2000 | Li et al. | |
| 6,127,597 A | 10/2000 | Beyar et al. | |
| 6,146,401 A | 11/2000 | Yoon et al. | |
| 6,149,664 A | 11/2000 | Kurz | |
| 6,187,015 B1 | 2/2001 | Brenneman | |
| 6,190,381 B1 | 2/2001 | Olsen et al. | |
| 6,214,016 B1 | 4/2001 | Williams et al. | |
| 6,228,068 B1 | 5/2001 | Yoon | |
| 6,228,082 B1 | 5/2001 | Baker et al. | |
| 6,325,812 B1 | * 12/2001 | Dubrul et al. | .............. 606/185 |
| 2002/0072768 A1 | * 6/2002 | Ginn | .................. 606/213 |

* cited by examiner

Primary Examiner—Kevin Shaver
Assistant Examiner—Michael B. Priddy
(74) Attorney, Agent, or Firm—Woodard, Emhardt, Moriarty, McNett & Henry LLP

(57) ABSTRACT

Instrumentation for treatment of the spine, including an elongate member having a deformable distal end portion at least partially formed of a flexible and preferably elastic material. The distal end portion has an initial configuration for placement adjacent a vertebral body and a deformed configuration defining at least one outwardly extending projection for displacement of at least a portion of the vertebral body. The elongate member preferably comprises a rod member, a sleeve member and an actuator mechanism for imparting relative linear displacement between the rod and sleeve members to effect outward deformation of the distal end portion of the sleeve member. In one embodiment, the instrumentation is used to compact cancellous bone to form a cavity within a vertebral body. In another embodiment, the instrumentation is used to reduce a compression fracture. In yet another embodiment, the instrumentation is used to distract a disc space between adjacent vertebral bodies.

51 Claims, 9 Drawing Sheets

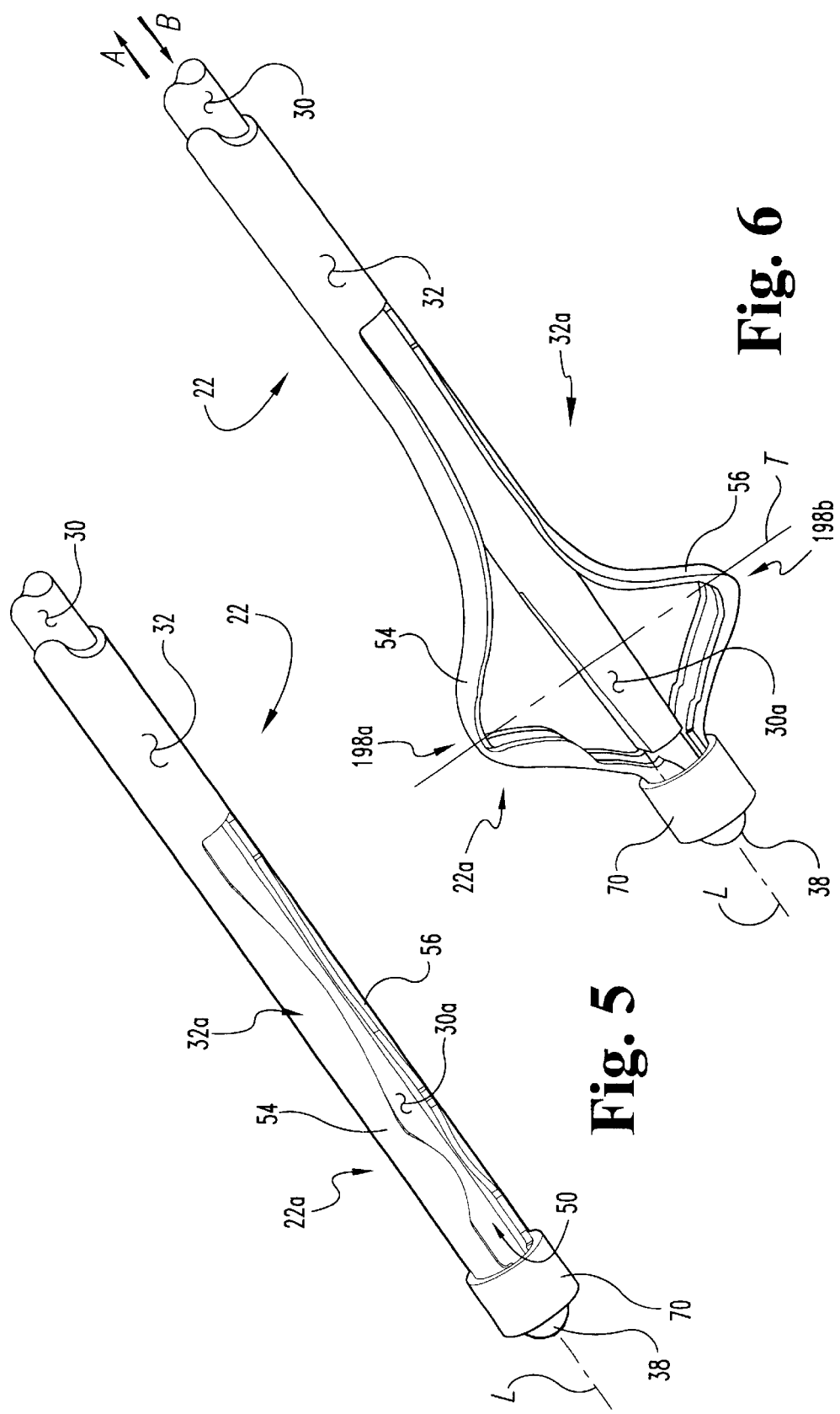

SURGICAL INSTRUMENTATION AND METHOD FOR TREATMENT OF THE SPINE

CROSS REFERENCE TO RELATED APPLICATIONS

The present application claims the benefit of Provisional Application Ser. No. 60/224,491, filed Aug. 11, 2000 and entitled Vertebral Plasty Reduction Device, the contents of which are hereby incorporated by reference in their entirety.

FIELD OF THE INVENTION

The present invention relates generally to the field of surgical instrumentation and methods for treatment of the spine, and more particularly relates to instrumentation and methods for transversely displacing structures associated with the spine.

BACKGROUND OF THE INVENTION

Various instruments and methods for the treatment of compression-type bone fractures and other osteoporotic and/or non-osteoporotic conditions have been developed. Such methods generally include a series of steps performed by a surgeon to correct and stabilize the compression fracture. A cavity is typically formed in the bone to be treated, followed by the insertion of an inflatable balloon-like device into the bone cavity. Inflation of the balloon-like device causes a compaction of the cancellous bone and/or bone marrow against the inner cortical wall of the bone, thereby resulting in enlargement of the bone cavity and/or reduction of the compression fracture. The balloon-like device is then deflated and removed from the bone cavity. A biocompatible filling material, such as methylmethacrylate cement or a synthetic bone substitute, is sometimes delivered into the bone cavity and allowed to set to a hardened condition to provide internal structural support to the bone.

While the above-described instruments and methods provide an adequate protocol for the treatment and fixation of compression-type bone fractures, it has been found that expansion of the balloon-like device is not controllable. Instead, when such balloon-like device is inflated, expansion occurs along a path of least resistance. As a result, the direction of compaction of the cancellous bone and/or reduction of the compression fracture is not controllable, and expansion occurs in multiple directions and along multiple axes.

Thus, there is a general need in the industry to provide surgical instrumentation and methods for use in treatment of the spine that provide a greater degree of control over transverse displacement of structures associated with the spine than is currently available within the industry. The present invention meets this need and provides other benefits and advantages in a novel and unobvious manner.

SUMMARY OF THE INVENTION

The present invention relates generally surgical instrumentation and methods for displacement of at least a portion of a vertebral body. While the actual nature of the invention covered herein can only be determined with reference to the claims appended hereto, certain forms of the invention that are characteristic of the preferred embodiments disclosed herein are described briefly as follows.

In one form of the present invention, instrumentation is provided for treatment of the spine, comprising an elongate member extending along a longitudinal axis and including a deformable distal end portion having an initial configuration for placement adjacent a spinal structure and a deformed configuration defining at least one transverse projection for transverse displacement of at least a portion of the spinal structure.

In another form of the present invention, instrumentation is provided for treatment of the spine, comprising a first member, a second member having a distal end portion engaged with the first member, with the distal end portion having an initial configuration for placement adjacent a spinal structure and an expanded configuration for displacement of at least a portion of the spinal structure, and wherein relative displacement between the first and second members causes the distal end portion to reform from the initial configuration toward the expanded configuration.

In yet another form of the present invention, instrumentation is provided for treatment of the spine, comprising a member including a deformable distal end portion having an initial configuration for positioning adjacent a spinal structure and a deformed configuration for displacing at least a portion of the spinal structure, and means for mechanically deforming the distal end portion from the initial configuration toward the deformed configuration to displace the spinal structure in at least one predetermined direction.

In still another form of the present invention, a method is provided for treatment of the spine, comprising providing an instrument including a distal end portion having an insertion configuration and a deformed configuration. The method further comprises positioning the distal end portion adjacent a spinal structure while in the insertion configuration and deforming the distal end portion toward the deformed configuration to displace at least a portion of the spinal structure.

It is one object of the present invention to provide improved surgical instrumentation and methods for treatment of the spine.

Further objects, features, advantages, benefits, and aspects of the present invention will become apparent from the drawings and description contained herein.

BRIEF DESCRIPTION OF THE DRAWINGS

FIG. 5 is a perspective view of the distal end portion of the surgical instrument depicted in FIG. 1, as shown in an initial configuration.

FIG. 6 is a perspective view of the distal end portion depicted in FIG. 5, as shown in a deformed configuration.

DESCRIPTION OF THE ILLUSTRATED EMBODIMENTS

Figure 1:
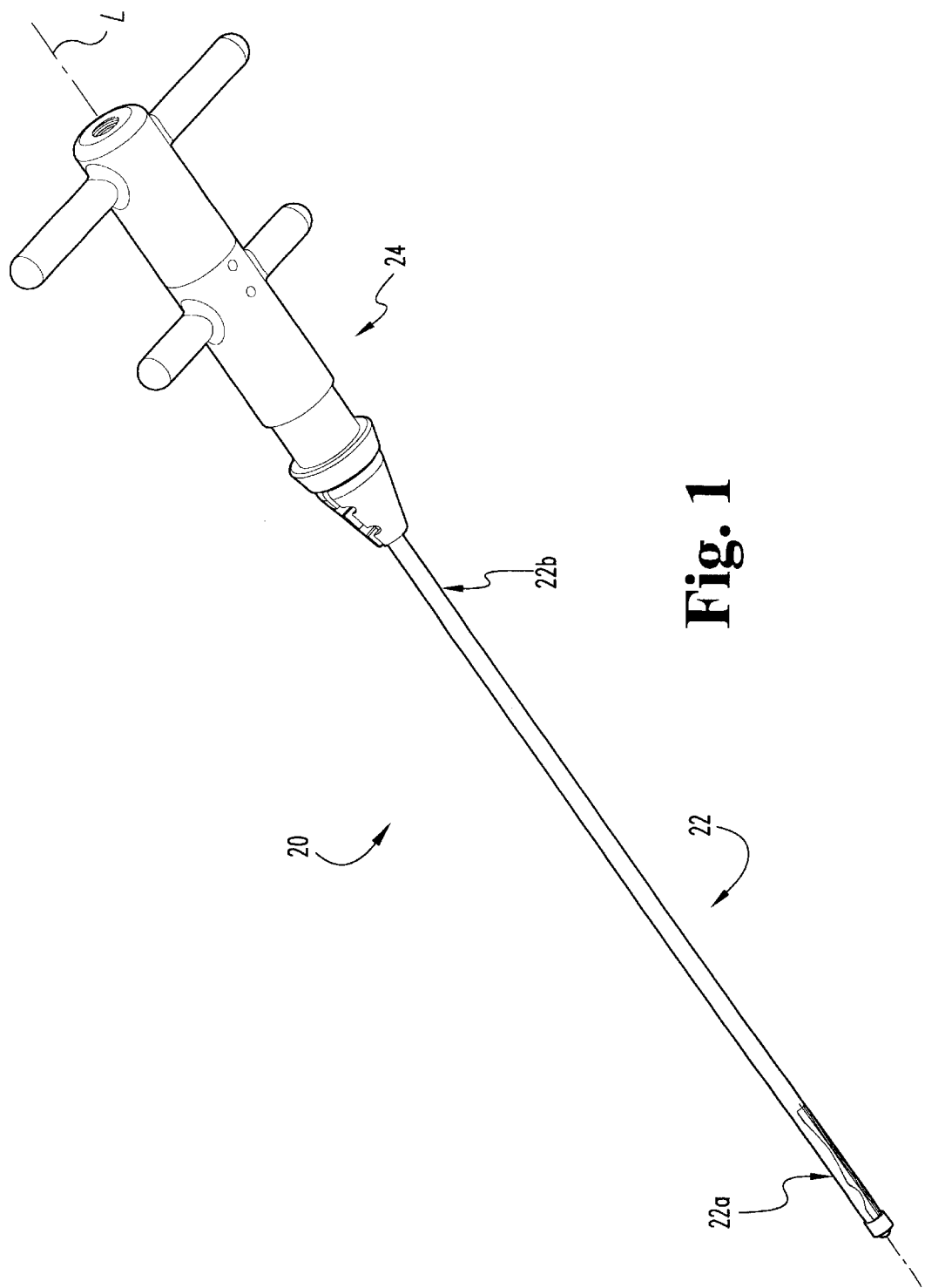
FIG. 1 is a perspective view of a surgical instrument according to one form of the present invention.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Referring to FIG. 1, shown therein is an instrument 20 for treatment of the spine according to one form of the present invention. Instrument 20 is particularly useful for placement adjacent a spinal structure and selective displacement of at least a portion of the spinal structure. In one embodiment of the invention, the spinal structure is a vertebral body. It should be understood that instrument 20 may be used in intrabody applications such as, for example, a vertebral plasty procedure to compact cancellous bone within the vertebral body and/or to reduce a compression fracture of the vertebral body. Additionally, it should be understood that instrument 20 may be used in interbody applications such as, for example, to distract a space between adjacent vertebral bodies, such as the vertebral disc space. It should further be understood that in other embodiments of the invention, the spinal structure may be comprised of a spinal implant such as, for example, a cage device, or any other structure used in association with treatment of the spine. Additionally, although instrument 20 is illustrated and described in the context of treatment of a human spine, it should be understood that instrument 20 may be used to treat other animals. It should further be understood that instrument 20 may be used in association with applications outside of the spinal field such as, for example, to treat other types of bony structures.

Instrument 20 is generally comprised of an elongate member 22 extending generally along a longitudinal axis L and having a distal end portion 22a and a proximal end portion 22b. Although the illustrated embodiment depicts elongate member 22 as having a generally linear, unitary configuration, it should be understood that elongate member 22 may take on other configurations as well, such as, for example, a curvilinear configuration or a hinged configuration. Instrument 20 also includes an actuator mechanism 24 coupled to the proximal end portion 22b of elongate member 22. As will be discussed in greater detail below, the distal end portion 22a is deformable and is configured to outwardly expand in response to a mechanically induced force. Such force may be effected, for example, by the selective actuation of actuator mechanism 24.

As shown in FIGS. 5 and 6, the distal end portion 22a is reformable between an initial configuration (FIG. 5) and a deformed configuration (FIG. 6). As used herein, the term "initial configuration" is broadly defined to encompass a structural configuration of elongate member 22 that is suitable for placement adjacent a spinal structure, and the term "deformed configuration" is broadly defined to encompass a structural configuration of elongate member 22 that is suitable for displacement of at least a portion of the spinal structure. As discussed above, in one embodiment of the invention, the spinal structure is a vertebral body, and displacement of the vertebral body could be associated with either intrabody or interbody applications.

Figure 2:
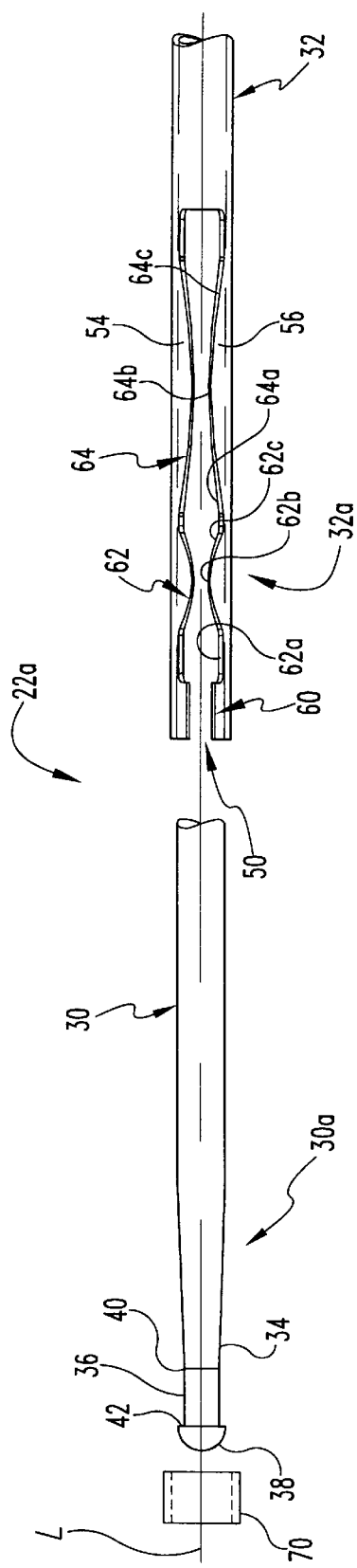
FIG. 2 is an exploded side view of a distal end portion of the surgical instrument depicted in FIG. 1.

Referring to FIG. 2, shown therein are further details regarding the elongate member 22, and more specifically the deformable distal end portion 22a of elongate member 22. In one embodiment of the invention, the elongate member 22 is comprised of an inner rod member 30 and an outer sleeve member 32. The inner rod 30 is preferably formed of a substantially rigid medical grade material such as, for example, titanium or stainless steel. The distal end portion 30a of rod 30 includes a tapered portion 34, a reduced cross-section intermediate portion 36, and a rounded distal end portion 38. In one embodiment, the intermediate portion 36 has a diameter somewhat smaller than the diameter of the tapered portion 34 and the rounded distal end portion 38 so as to define a pair of opposing shoulders 40, 42. Although rod 30 has been illustrated and described as having a substantially circular cross section, it should be understood that other shapes and configurations are also contemplated as being within the scope of the invention including, for example, elliptical, square, rectangular or other polygonal configurations.

The outer sleeve 32 preferably has a tubular configuration defining an inner passage extending therethrough generally along longitudinal axis L and sized to slidably receive rod 30. Sleeve 32 is preferably formed of a flexible material that is capable of facilitating deformation from an initial configuration toward a deformed configuration. Additionally, sleeve 32 is preferably formed of an elastic material that is capable of facilitating elastic deformation from the initial configuration toward the deformed configuration and reformation back toward the initial configuration. Sleeve 32 may be formed of materials including, but not limited to, titanium, stainless steel, an elastomer, a polymer, a rubber, a composite material or a shape-memory material. Although the entire length of sleeve 32 may be formed of a flexible, elastic material, it should be understood that only the distal end portion 32a of sleeve 32 need be formed of such material, with the remainder of sleeve 32 being formed of any suitable medical grade material. Moreover, although outer sleeve 32 is illustrated as having a substantially tubular configuration, it should be understood that other shapes and configurations of sleeve 32 are also contemplated as being within the scope of the present invention. Additionally, although sleeve 32 has been illustrated and described as being formed as a single-piece, unitary structure, it should be understood that the distal end portion 32a could be formed separately from the remainder of sleeve 32, and coupled together by any known method, such as, for example, by fastening, welding or adhesion.

The distal end portion 32a of sleeve 32 includes at least one slot 50 extending generally along longitudinal axis L, and preferably includes at least a pair of slots 50 and 52 (not shown) disposed generally opposite one another so as to define a pair of longitudinally extending flexible strips of material 54, 56. It should be understood, however, that the distal end portion 32a of sleeve 32 could be configured to define any number of longitudinally extending slots, including three or more slots, which would in turn define a corresponding number of longitudinally extending flexible strips of material. It should further be understood that distal end portion 32a may include a number of slots disposed at various axial locations along longitudinal axis L. As will be described below, the slots 50, 52 are provided to facilitate outward buckling of the distal end portion 32a of sleeve 32 in at least one predetermined direction upon the selective actuation of the actuator mechanism 24.

In the illustrated embodiment, the slots 50, 52 are substantially identical in shape and configuration, and thus only slot 50 will be described in detail. However, it should be understood that slots 50, 52 may take on different shapes and configurations. Slots 50, 52 and strips of material 54, 56 are illustrated as having a predetermined shape to provide a degree of control over the outward buckling of the strips of material 54, 56. In one embodiment of the invention, the slots 50, 52 and strips of material 54, 56 have an irregular shape. Slot 50 includes a relatively narrow and straight slot portion 60, a first hourglass-shaped slot portion 62 formed by a first series of arcuate portions, and a second hourglass-shaped slot portion 64 formed by a second series of arcuate portions. As will become apparent below, the widened areas of the hourglass-shaped portions 62 and 64 serve as bending or flexion points to control the outward deformation of the flexible strips of material 54, 56.

The straight slot portion 60 extends longitudinally from the distal end of sleeve 32. The first hourglass-shaped portion 62 extends longitudinally from slot portion 60 and includes a first widened area 62a, a narrowed area 62b, and a second widened area 62c. The second hourglass-shaped portion 64 extends longitudinally from the first hourglass-shaped portion 62 and includes a first widened area 64a, a narrow area 64b, and a second widened area 64c. Although a specific configuration of slots 50, 52 have been illustrated and described, it should be understood that other shapes and configuration of slots 50, 52 are also contemplated as falling within the scope of the invention.

In one embodiment of the invention, the distal end portion 32a of sleeve 32 is secured to the inner rod 30 by way of a compression ring 70. Specifically, the distal-most portion of sleeve 32 is disposed about portion 36 of rod 30, with the distal end of sleeve 32 abutting the shoulder 42 formed by the rounded distal end portion 38. The compression ring 70 is positioned about the distal-most portion of sleeve 32 and is compressed thereabout, such as, for example, by mechanical crimping to secure sleeve 32 to inner rod 30. As should be appreciated, slot portion 60 aids in tightly compressing sleeve 32 about inner rod 30 to provide secure engagement therebetween. It should be understood that compression ring 70 could alternatively be compressed about distal-most portion of sleeve 32 by other means, such as, for example, by forming compression ring 70 out of a shape-memory material that is reformable to a memorized configuration having an internal diameter that is less than the outer diameter of sleeve 32. It should further be understood that the distal-most end portion of sleeve 32 could be secured to rod 30 by other means, such as, for example, by fastening, welding, adhesion or other methods of attachment known to those of skill in the art.

Figure 3:
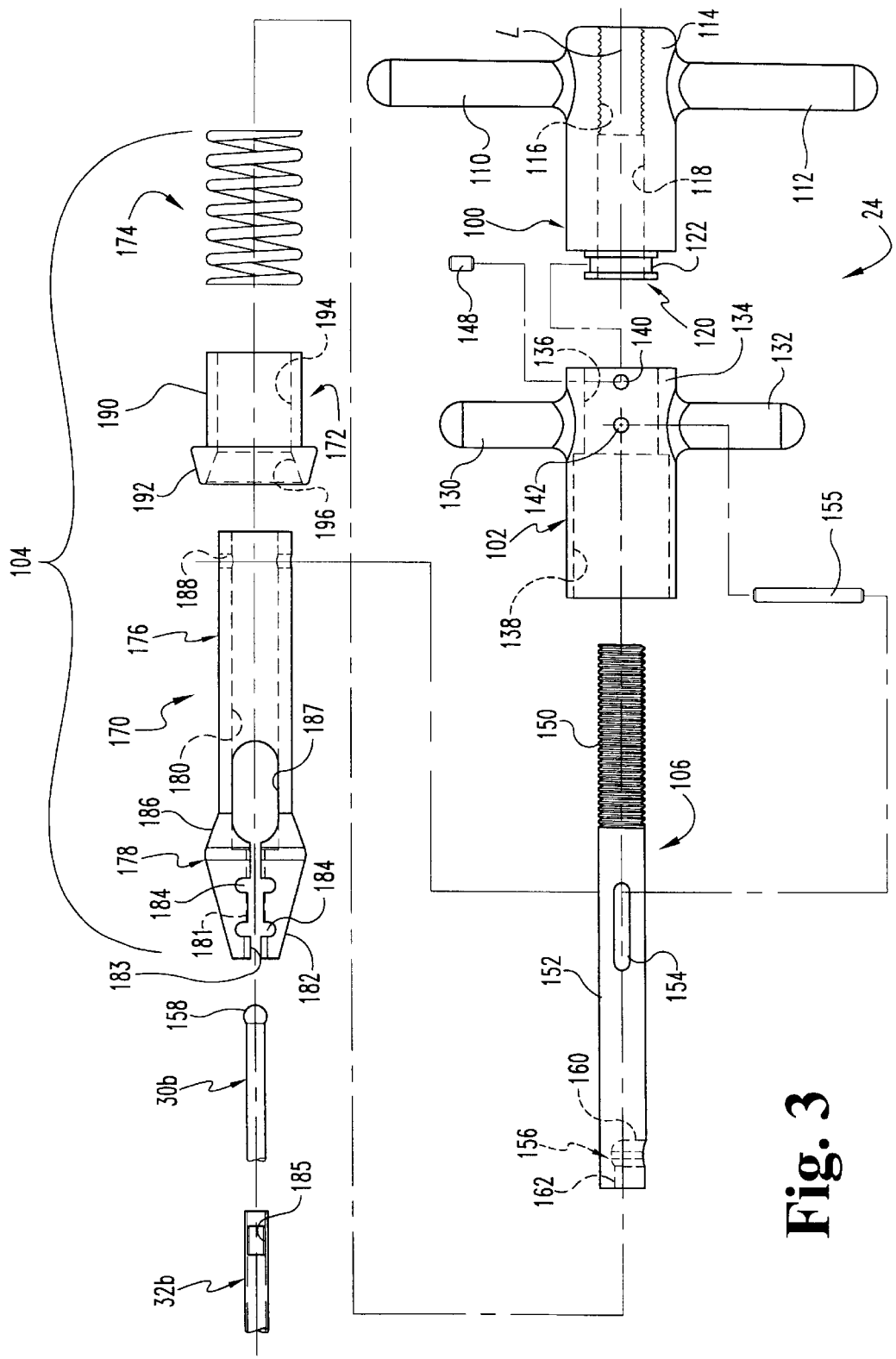
FIG. 3 is an exploded side view of a proximal end portion of the surgical instrument depicted in FIG. 1.
Figure 4:
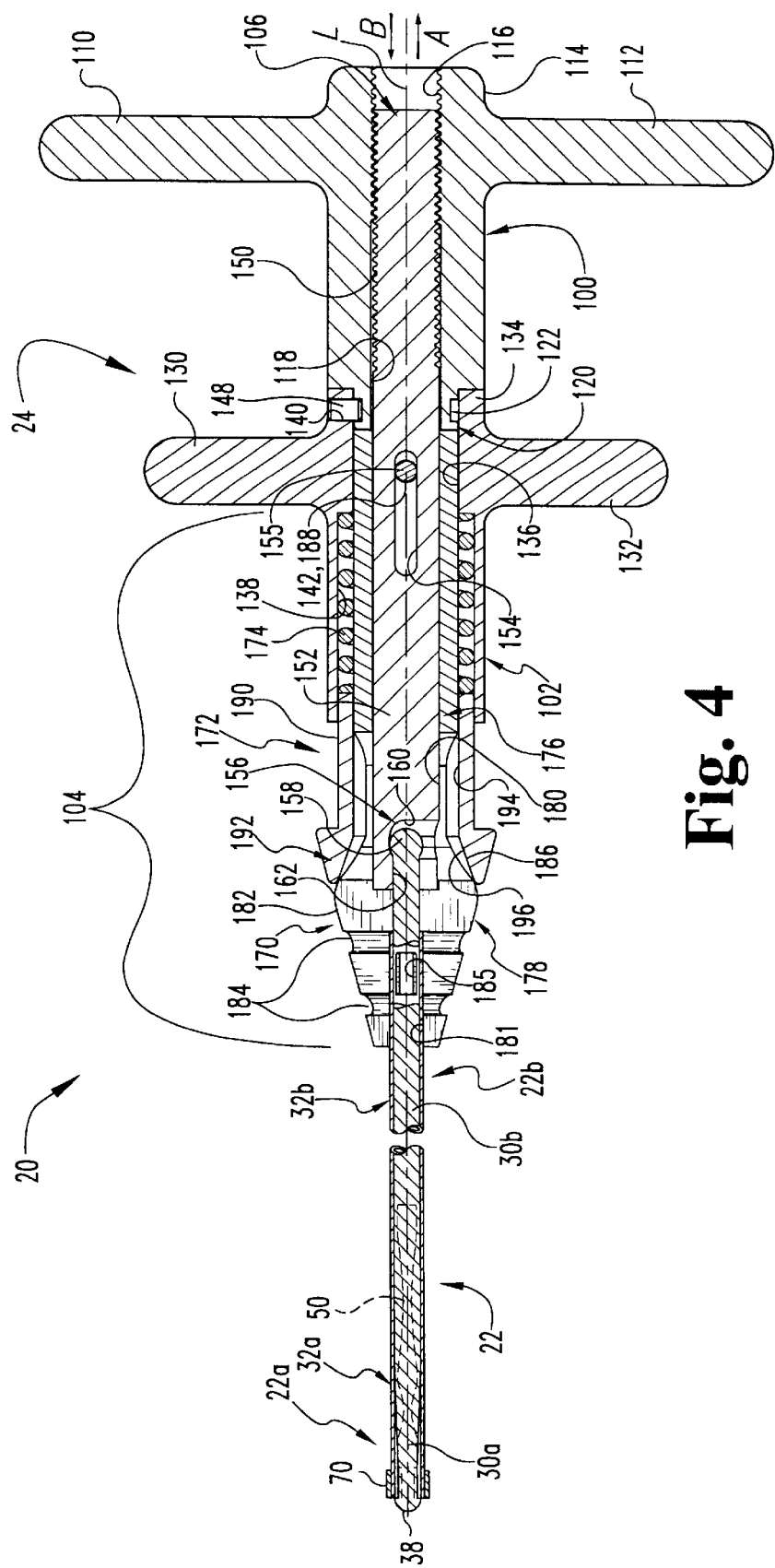
FIG. 4 is a broken cross-sectional side view of the surgical instrument depicted in FIG. 1.

Referring to FIGS. 3 and 4, shown therein are further details regarding the actuator mechanism 24. Actuator mechanism 24 is generally comprised of a rotary handle 100, a stationary handle 102, a connector assembly 104, and an actuator member 106. As will be discussed in further detail below, the connector assembly 104 is configured to secure the elongate member 22, and more specifically the outer sleeve 32, to the remainder of the actuator mechanism 24. As will also be discussed below, the threaded actuator member 106 is coupled to the inner rod 30 and is engaged with the rotary handle 100 such that rotational displacement of handle 100 about longitudinal axis L linearly displaces the actuator member 106 along longitudinal axis L. As described above, the linear displacement of rod 30 relative to sleeve 32 causes the distal end portion 32a of sleeve 32 to reform from its initial configuration toward its deformed configuration.

The rotary handle 100 includes a pair of lateral extensions 110, 112 extending outwardly from a main body portion 114 to define a T-handle arrangement which aids the surgeon in rotating the handle 100 relative to the stationary handle 102. The main body portion 114 includes an opening extending along longitudinal axis L and having a threaded portion 116 and an unthreaded portion 118. A hub portion 120 extends from the main body portion 114 and defines an annular groove 122.

The stationary handle 102 includes a pair lateral extensions 130, 132 extending outwardly from a main body portion 134 to define a second T-handle arrangement which aids the surgeon in securely gripping instrument 20 and in maintaining the handle 102 in a stationary rotational position during rotation of handle 100. The main body portion 134 includes an opening extending therethrough along longitudinal axis L and defining a first cavity 136 and a second cavity 138. A pair of openings 140, 142 extend through the main body portion 134 and are disposed in communication with the first cavity 136. The hub portion 120 of handle 100 is inserted within the first cavity 136 and a pin or fastener 148 is inserted through opening 140 and positioned within the annular groove 122 to axially couple rotary handle 100 to stationary handle 102 while permitting relative rotational displacement therebetween.

The actuator member 106 includes a threaded shank portion 150 and an unthreaded shank portion 152. The threaded shank portion 150 is configured to threadingly engage the threaded opening 116 in rotary handle 100. In one embodiment of the invention, the threaded shank portion 150 and the threaded opening 116 each define right hand threads. The unthreaded shank portion 152 includes a slotted opening 154 extending therethrough that is aligned with the opening 142 in the stationary handle 102. A pin or fastener 155 is inserted through the opening 142 and the slotted opening 154 to couple the actuator member 106 to the stationary handle 102. As should be apparent, pin 155 substantially prevents relative rotational displacement between actuator member 106 and handle 102 while allowing a limited amount of relative linear displacement along longitudinal axis L. The distal end portion of the actuator member 106 includes a socket 156 configured to accept a corresponding ball portion 158 extending from the proximal end portion 30b of rod 30. The socket opening 156 includes a spherical portion 160 sized to receive the ball portion 158 therein, and a cylindrical portion 162 sized to receive the distal end portion 30b of rod 30 therethrough to connect rod 30 to actuator member 106. It should be understood, however, that other methods of interconnecting rod 30 and actuator member 106 are also contemplated as would occur to one of skill in the art.

As discussed above, the connector assembly 104 is configured to connect the elongate member 22, and more specifically the outer sleeve 32, to the remainder of the actuator mechanism 24. The connector assembly 104 is generally comprised of a gripper member 170, a lock collar member 172 and a biasing member 174. The gripper member 170 includes a connecting segment 176, a gripping segment 178 and a longitudinal passage having a first portion 180 extending through connecting segment 176 and a second portion 181 extending through the gripping segment 178. The first portion 180 of the passage is sized to receive the shank portion 152 of actuator member 150 therein, and the second portion 181 of the passage is sized to receive the proximal end portion 32b of sleeve 32 therein.

The gripping segment 178 of gripper member 170 has a generally conical shape and includes a tapered outer surface 182. The gripping segment 178 also includes a longitudinally extending slit 183 and a pair of transverse slots 184 that intersect slit 183, with both the slit 183 and the slots 184 intersecting the longitudinal passage 181. One purpose of the slit 183 and the slots 184 is to facilitate compression of the gripping segment 178 about the proximal end portion 32b of sleeve 32. The proximal end portion 32b of sleeve 32 defines an opening or window 185 extending therethrough to further facilitate gripping of sleeve 32 by gripping segment 178. Another purpose of slit 183 is to provide a passageway for the lateral insertion of the proximal end portion 30b of rod 30 therethrough to permit assembly with the actuator member 106. The gripping segment 178 also includes an outer tapered surface 186, the purpose of which will become evident below.

The connecting segment 176 of gripper member 170 defines an elongate opening 187 extending transversely therethrough and being positioned in communication with the longitudinal slit 183. One purpose of the elongate opening 187 is to facilitate compression of the gripping segment 178 about the proximal end portion 32b of sleeve 32. Another purpose of the transverse slot 187 is to provide a passageway for the lateral insertion of the ball portion 158 of rod 30 therethrough and into engagement with the socket 156 defined in actuator member 106. The connecting segment 176 also includes an opening 188 extending transversely therethrough and aligned with the opening 142 in the stationary handle 102. Pin 155 is inserted through the opening 188 to axially couple the gripper member 170, and in turn the elongate member 22, to the stationary handle 102 in a manner that substantially prevents relative linear and rotational displacement therebetween.

The lock collar member 172 includes a cylindrically-shaped body portion 190, a tapered end portion 192, and a longitudinal passage 194 extending therethrough and being sized to receive the connecting segment 176 of gripper member 170 therein. The cylindrical body portion 190 is sized to be received within cavity 138 of stationary handle 102. The longitudinal passage 194 includes an inner tapered surface 196 that corresponds to the outer tapered surface 186 of gripping segment 178. In one embodiment of the invention, the biasing member 174 is a coil spring. However, it should be understood that other types of biasing devices may alternatively be used as would occur to one of skill in the art.

Referring to FIG. 4, spring 174 is disposed within the cavity 138 of stationary handle 102 and is engaged against the proximal end of the lock collar 172 to bias the lock collar 172 toward the gripping segment 178. The biasing of lock collar 172 engages the tapered inner surface 196 tightly against the tapered outer surface 186 of gripping segment 178. Such engagement creates an inward compression force onto the gripping segment 178 which causes the gripping segment 178 to collapse tightly about the proximal end portion 32b of sleeve 32 to securely grip sleeve 32 within the longitudinal passage 181. The tapered outer surface 192 of lock collar 172 is oriented at about the same angle as the tapered outer surface 182 of gripping segment 178 to provide a relatively smooth transition between lock collar 172 and gripping segment 178.

Based on the above description and corresponding illustrations, it should be apparent that rotation of handle 100 relative to stationary handle 102 in a clockwise direction (assuming right hand threading) will cause the actuator member 106 to be linearly displaced in the direction of arrow A, which will correspondingly cause rod 30 to be linearly displaced in the direction of arrow A. Furthermore, since the distal end portion of sleeve 32 is engaged with the distal end portion of rod 30, linear displacement of rod 30 in the direction of arrow A will cause the deformable distal end portion 32a of sleeve 32 to buckle outwardly toward the deformed configuration illustrated in FIG. 6. It should also be apparent that rotation of handle 100 relative to stationary handle 102 in a counter-clockwise direction will cause the actuator member 106 to be linearly displaced in the direction of arrow B, which will correspondingly cause rod 30 to be linearly displaced in the direction of arrow B. Linear displacement of rod 30 in the direction of arrow B will cause the deformable distal end portion 32a of sleeve 32 to reform back toward the insertion configuration illustrated in FIG. 5. As should be apparent, instead of rotating handle 100 relative to handle 102 to impart relative linear displacement between rod 30 and sleeve 32, it is also possible to hold handle 100 in a stationary position and to rotate handle 102 relative to handle 100 to impart relative linear displacement between rod 30 and sleeve 32.

Although one specific embodiment of the actuator mechanism 24 has been illustrated and described herein, it should be understood that the use of other types and configurations of actuator mechanisms are also contemplated as would occur to one of skill in the art. As should be apparent, any type of actuator mechanism that is capable of imparting relative displacement between rod 30 and sleeve 32 to reform the distal end portion 32a of sleeve 32 between the initial and deformed configurations may be used. It should further be understood that in an alternative form of the invention, rod 30 may be manually displaced by the surgeon relative to sleeve 32, thereby eliminating the need for a separate actuator mechanism 24.

Referring now to FIGS. 5 and 6, shown therein is the distal end portion 22a of elongate member 22, as shown in an initial insertion configuration and a mechanically deformed expanded configuration, respectively. When in the initial configuration (FIG. 5), the distal end portion 32a of sleeve 32 has a relatively low profile to facilitate positioning adjacent a vertebral body. As should be appreciated, the rounded distal end portion 38 reduces the likelihood of damage to adjacent tissue during such positioning. As used herein, positioning of the distal end portion 32a adjacent a vertebral body is meant to include positioning of the distal end portion 32a in proximity to a vertebral body, within a vertebral body or within a space between adjacent vertebral bodies. As discussed above, instrument 20 may also be used in association with spinal structures other than a vertebral body, such as, for example, a spinal implant, with the distal end portion 32a of sleeve 32 being positioned adjacent or within the spinal implant when in the insertion configuration.

Once properly positioned adjacent the vertebral body, the distal end portion 32a of sleeve 32 is mechanically deformed by displacing the rod 30 relative to the sleeve 32. In the illustrated embodiment of the invention, such relative displacement is accomplished by linearly displacing rod 30 relative to sleeve 32 in the direction of arrow A, and is initiated by the selective actuation of actuator mechanism 24. In an alternative embodiment of the invention, the distal end portion 32a of sleeve 32 may be mechanically deformed toward the expanded configuration by way of relative rotational displacement between rod 30 and sleeve 32.

When reformed toward the expanded configuration (FIG. 6), the distal end portion 32a of sleeve 32 is outwardly deformed relative to longitudinal axis L so as to form a number of laterally extending projections or protrusions 198a, 198b. As discussed above, the deformed configuration of instrument 20 may define any number of laterally extending projections, including a single projection or three or more projections, and may define a number of laterally extending projections at various axial locations along longitudinal axis L. It should be apparent that the number, position, and direction of the laterally extending projections is at least partially controlled by the configuration and placement of the slots 50 in sleeve 32. In this manner, formation of the laterally extending projections and the resulting displacement of the vertebral body is said to be directionally controlled. Moreover, if the deformed configuration of instrument 20 defines a single projection 198a, or a single pair of opposing projections 198a, 198b aligned along a common transverse axis T, then formation of the laterally extending projection and the resulting displacement of the vertebral body is said to be uniaxial. Further, if the deformed configuration of instrument 20 defines a single projection 198a extending in a single direction, then formation of the laterally extending projection and the resulting displacement of the vertebral body is said to be unidirectional.

Following displacement of the vertebral body, the distal end portion 32a of sleeve 32 may be reformed from its deformed/expanded configuration back toward its initial insertion configuration by linearly displacing rod 30 relative to sleeve 32 in the direction of arrow B. As discussed above, the distal end portion 32a of sleeve 32 may be formed of a shape-memory material, such as, for example, a shape-memory alloy ("SMA") to aid in reforming the distal end portion 32a from the deformed configuration back toward its initial configuration. More specifically, SMAs are known to exhibit a characteristic or behavior in which a particular component formed of an SMA is capable of being deformed from an initial "memorized" shape or configuration to a different shape or configuration, and then reformed back toward its initial shape or configuration.

The ability to possess a shape-memory characteristic or behavior is a result of the fact that the SMA undergoes a reversible transformation from an austenitic state to a martensitic state. If the martensitic transformation occurs due to the imposition of stress, the shape-memory phenomena is referred to as stress-induced martensitic transformation. As a result, SMAs are known to display a superelastic or rubber-like behavior in which a strain attained beyond the elastic limit of the SMA material during loading is recovered during unloading. This superelastic phenomena occurs when stress is applied to an SMA article at a temperature slightly higher than the temperature at which the SMA begins to transform into austenite (sometimes referred to as the transformation temperature or $A_s$). When stressed, the article first deforms elastically up to the yield point of the SMA material (sometimes referred to as the critical stress). However, upon the further imposition of stress, the SMA material begins to transform into stress-induced martensite. This transformation takes place at an essentially constant stress, up to the point where the SMA material is completely transformed into martensite. When the stress is removed, the SMA material will revert back into austenite and the article will automatically return toward its original, pre-programmed or memorized shape without a corresponding change in temperature.

Further details regarding the superelastic phenomena of a SMA and additional characteristics of stress-induced martensite are more fully described by Yuichi Suzuki in an article entitled Shape Memory Effect and Super-Elasticity in Ni—Ti Alloys, Titanium and Zirconium, Vol. 30, No. 4, Oct. 1982, the contents of which are hereby incorporated by reference. Additionally, while there are many alloys that exhibit shape-memory or superelastic characteristics, one of the more common SMAs is an alloy of nickel and titanium. One such well-known SMA is Nitinol®, which has proven to be highly effective for devices to be placed within the human body because its transformation temperature range generally falls between room temperature and normal human body temperature (i.e., at about 35–40 degrees Celsius). Moreover, Nitinol® has a very low corrosion rate and excellent wear resistance, thereby providing an advantage when used as a support structure within the human body. Additionally, implant studies in animals have shown minimal elevations of nickel in the tissues in contact with the Nitinol® material. It should be understood, however, that other SMA materials that exhibit superelastic characteristics are contemplated as being within the scope of the invention.

If the distal end portion 32b of outer sleeve 32 is formed of an SMA material and is reshaped or deformed while at a temperature above the transformation temperature $A_s$, of the SMA, the distal end portion 32b will automatically recover or reform toward its initial shape or configuration when the stress is removed from distal end portion 32b. As illustrated in FIG. 5, when distal end portion 32b is in its unstressed initial configuration, virtually all of the SMA material will be in an austenitic state. However, upon the imposition of stress onto distal end portion 32b (e.g., by turning actuator handle 100 in a clockwise direction relative to stationary handle 102), at least a portion of the SMA material will transform into reversible stress-induced martensite as the distal end portion 32b is deformed toward the expanded configuration. Upon the reduction or removal of the stress (e.g., by turning actuator handle 100 in a counter clockwise direction), at least a portion of the SMA material will be transformed back into austenite and the distal end portion 32b will automatically reform back toward the initial configuration.

Figure 7:
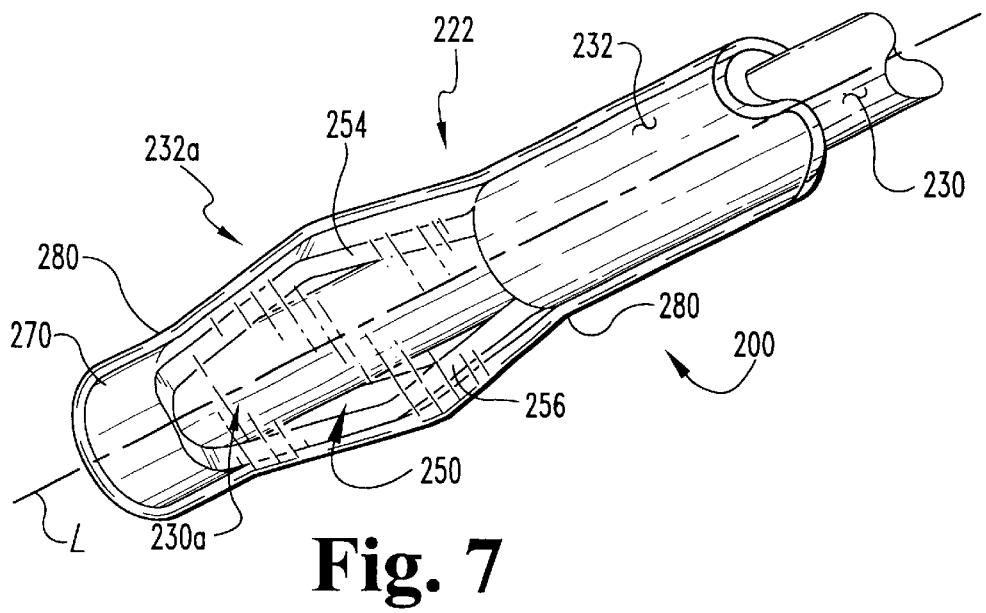
FIG. 7 is a perspective view of the distal end portion of a surgical instrument according to another form of the present invention, as shown in an initial configuration.
Figure 8:
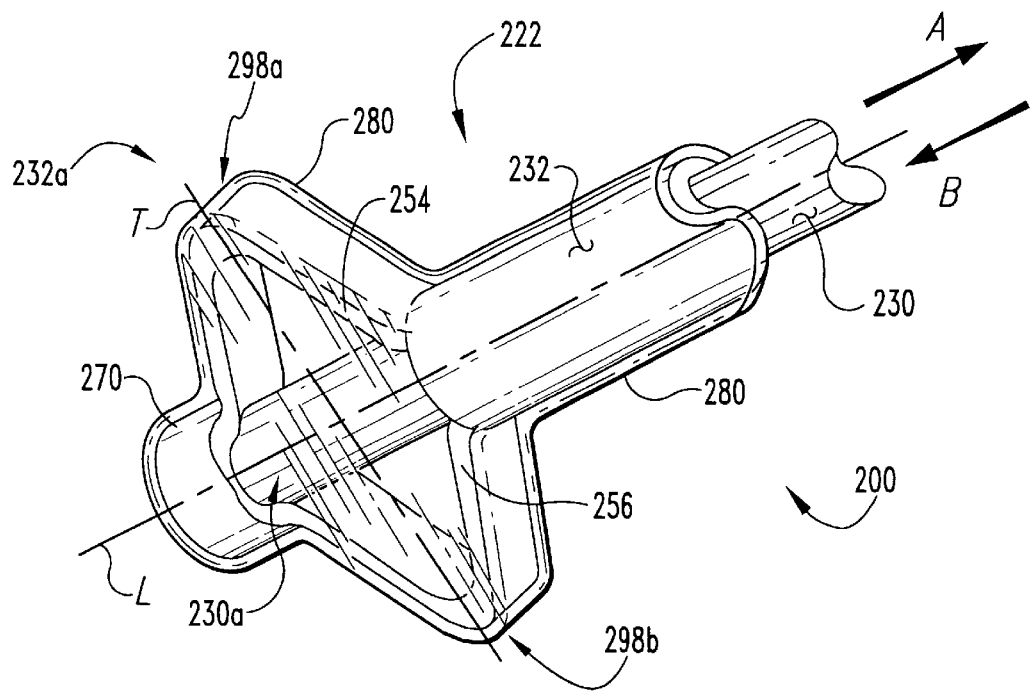
FIG. 8 is a perspective view of the distal end portion depicted in FIG. 7, as shown in a deformed configuration.

Referring now to FIGS. 7 and 8, shown therein is the distal end portion of an instrument 200 according to another form of the present invention, as shown in an initial insertion configuration and a mechanically deformed configuration, respectively. It should be understood that instrument 200 may be used in association with applications similar to those discussed above with regard to instrument 20, including both intrabody and interbody applications involving displacement of at least a portion of a vertebral body.

Instrument 200 is generally comprised of an elongate member 222 extending along a longitudinal axis L and having a distal end portion (as shown) and a proximal end portion (not shown) coupled to an actuator mechanism which may be configured similar to actuator mechanism 24. The distal end portion of elongate member 222 is deformable and is configured to outwardly expand in response to a mechanically induced force. Specifically, the distal end portion is reformable between an initial configuration (FIG. 7) for positioning adjacent a vertebral body, and a deformed configuration (FIG. 8) for displacement of at least a portion of the vertebral body. Although the illustrated embodiment depicts elongate member 222 as having a generally linear, unitary configuration, it should be understood that elongate member 222 may take on other configurations as well, such as, for example, a curvilinear configuration or a hinged configuration.

In the illustrated embodiment of instrument 200, the elongate member 222 is generally comprised of an inner rod member 230 and an outer sleeve member 232. The inner rod 230 is preferably formed of a substantially rigid medical grade material such as, for example, titanium or stainless steel. The rod 230 includes a distal end portion 230a that is disposed within and coupled to a distal end portion 232a of sleeve 232. Although rod 230 has been illustrated and described as having a substantially circular cross, it should be understood that other shapes and configurations are also contemplated as being within the scope of the present invention, such as, for example, elliptical, square, rectangular or other polygonal configurations.

The outer sleeve 232 preferably has a tubular configuration defining an inner passage extending therethrough generally along longitudinal axis L and sized to slidably receive rod 230 therein. Sleeve 232 is formed of a relatively flexible material that is capable of being reformed from an initial configuration to an expanded configuration. Preferably, sleeve 232 is formed of a relatively elastic material that is capable of being elastically deformed to the expanded configuration and reformed back toward the initial configuration. Sleeve 232 may be formed of materials including, but not limited to, titanium, stainless steel, an elastomer, a polymer, a rubber, a composite material or a shape-memory material. Although the entire length of sleeve 232 may be formed of a flexible, elastic material, it should be understood that only the distal end portion 232a need be formed of such material, with the remainder of sleeve 232 being formed of any suitable medical grade material. Additionally, although sleeve 232 is illustrated as having a substantially cylindrical or tubular configuration, it should be understood that other shapes and configurations of sleeve 232 are also contemplated as being within the scope of the present invention. Furthermore, although sleeve 232 has been illustrated and described as being formed as a single-piece, unitary structure, it should be understood that the distal end portion 232a could be formed separately from the remainder of sleeve 232, and coupled together by any known method, such as, for example, by fastening, welding or adhesion.

In one embodiment of instrument 200, the distal-most end portion 270 of sleeve 232 is secured to the distal end portion 230a of rod 230 by way of crimping. In other embodiments, sleeve portion 270 may be connected to rod portion 230a by a compression ring similar to compression ring 70, or by other connection techniques such as, for example, fastening, welding, adhesion, or other methods of attachment known to those of skill in the art.

The distal end portion 232a of sleeve 232 includes at least one rectangular-shaped window or slot 250 extending generally along longitudinal axis L, and preferably includes at least a pair of slots 250 and 252 (not shown) disposed generally opposite one another so as to define a pair of longitudinally extending flexible strips of material 254, 256. However, it should be understood that the distal end portion 232a of sleeve 232 could define any number of longitudinally extending slots, including three or more slots, which would in turn define a corresponding number of flexible strips of material disposed between the slots. The slots 250, 252 are provided to facilitate outward buckling of the distal end portion 232a of sleeve 232 upon the imposition of relative linear displacement between rod 230 and sleeve 232. As illustrated in FIG. 8, when reformed toward the expanded configuration, the flexible strips of material 254, 256 will outwardly buckle along transverse axis T at a location adjacent the midpoint of slots 250, 252. In the illustrated embodiment of instrument 200, the slots 250, 252 are substantially identical in shape and configuration. However, it should be understood that slots 250, 252 may take on different predetermined shapes and configurations. Additionally, although slots 250, 252 and strips of material 254, 256 are illustrated as having a generally rectangular shape, other predetermined shapes and configurations are also contemplated.

When in the initial configuration (FIG. 7), the distal end portion 232a of sleeve 232 has a relatively low profile to facilitate positioning adjacent a vertebral body. However, once properly positioned adjacent the vertebral body, the distal end portion 232a is mechanically deformed by displacing rod 230 relative to sleeve 232. In the illustrated embodiment, such relative displacement is accomplished by linearly displacing rod 230 relative to sleeve 232 in the direction of arrow A. In an alternative form of the present invention, the distal end portion 232a of sleeve 232 may be mechanically deformed toward the expanded configuration by way of relative rotational displacement between rod 230 and sleeve 232.

When reformed toward the expanded configuration (FIG. 8), the distal end portion 232a of sleeve 232 is outwardly deformed relative to longitudinal axis L so as to form a number of laterally extending projections or protrusions 298a, 298b. As discussed above, the deformed/expanded configuration of instrument 200 may alternatively define any number of laterally extending projections, including a single projection or three or more projections. Similar to instrument 20, formation of the laterally extending projections and the resulting displacement of the vertebral body by instrument 200 is directionally-controlled, and can be uniaxial, unidirectional or both uniaxial and unidirectional. Following displacement of the vertebral body, the distal end portion 232a of sleeve 232 may be reformed back toward its initial insertion configuration by linearly displacing rod 230 relative to sleeve 232 in the direction of arrow B. As discussed above with regard to instrument 20, the distal end portion 232a of sleeve 232 may be formed of a shape-memory material, such as, for example, a shape-memory alloy to aid in reforming distal end portion 232a back toward its initial configuration.

In one embodiment of the invention, at least the distal end portion of the elongate member 222 is covered by a flexible membrane 280. The flexible membrane 280 is preferably formed of a resilient material that is capable of conforming to the shape of the distal end portion 232a of sleeve 232 during reformation between the initial and deformed configurations. Such flexible materials include, but are not limited to, silicone, latex, rubber, a polymer or other suitable elastomeric materials. One purpose of the flexible membrane 280 is to prevent tissue or other foreign material from passing through the slots 250, 252 and being deposited within the space between the strips of material 254, 256 and the rod 230 and/or between the rod 230 and the remainder of the sleeve 232. As should be appreciated, such a build-up of tissue or foreign material may block or otherwise inhibit reformation of the distal end portion 232a of sleeve 232 from the deformed configuration (FIG. 8) back toward the initial configuration (FIG. 7). Although the flexible membrane 280 is illustrated as covering the distal end portion of elongate member 222, it should be understood that the flexible membrane 280 could be sized to cover the entire length of the elongate member 222. It should also be understood that a flexible membrane similar to flexible membrane 280 may be used in association with the surgical instrument 20 discussed above and/or the surgical instrument 300 discussed below.

Figure 9:
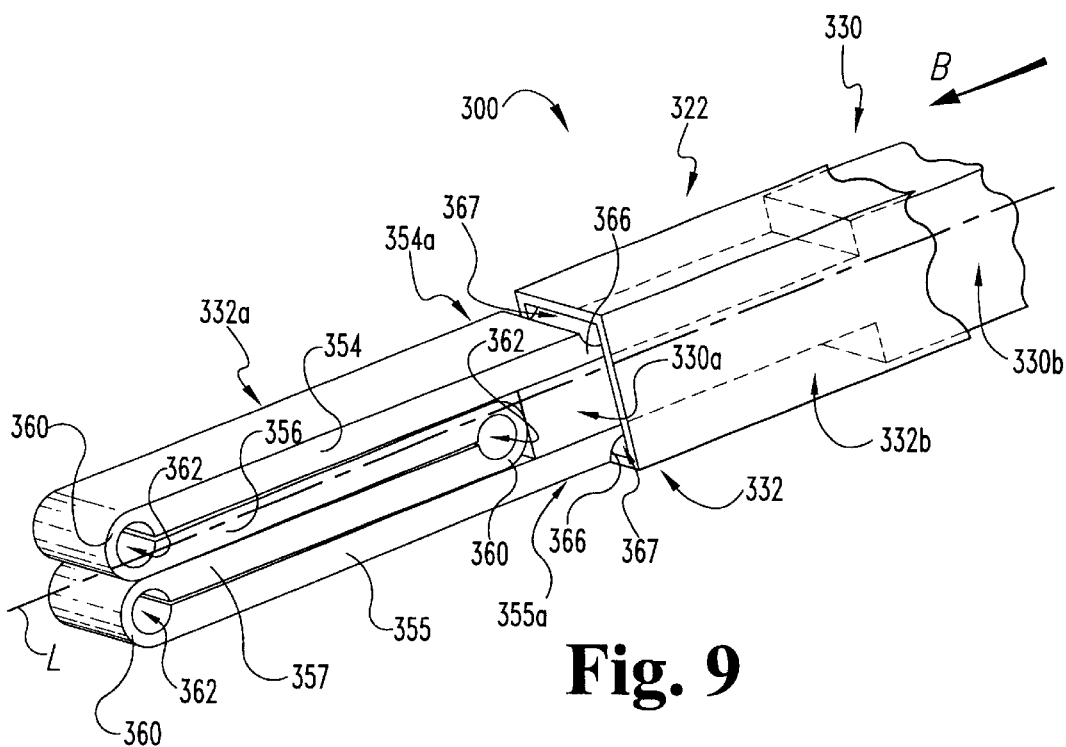
FIG. 9 is a perspective view of the distal end portion of a surgical instrument according to another form of the present invention, as shown in an initial collapsed configuration.
Figure 10:
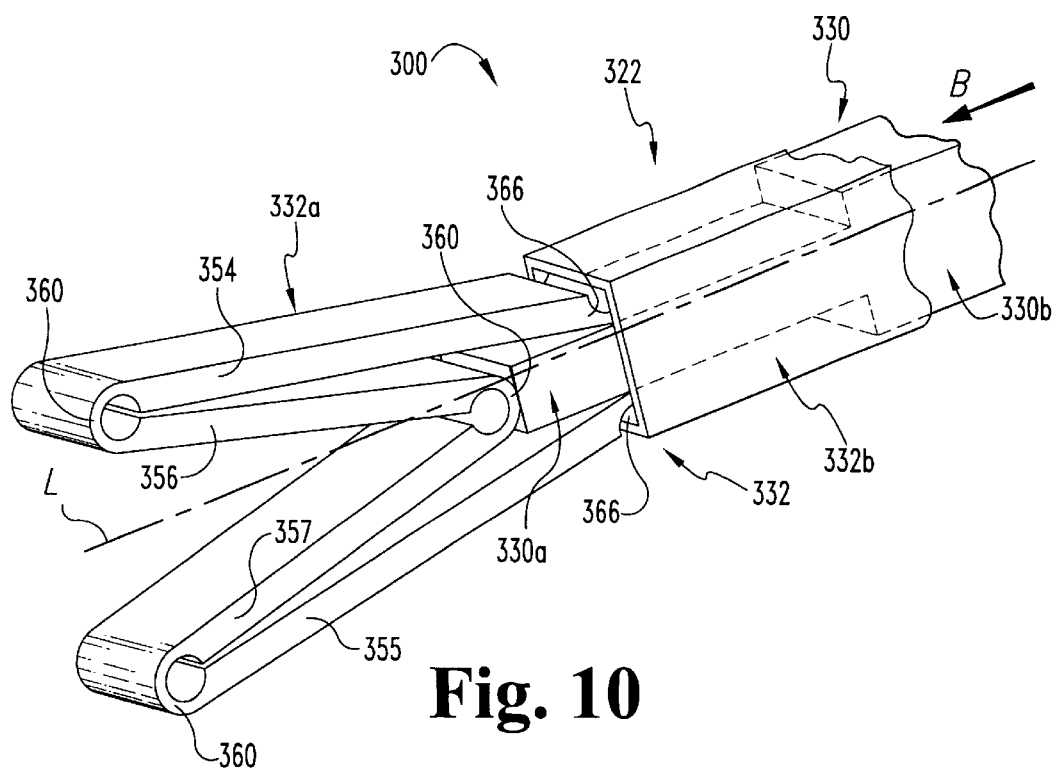
FIG. 10 is a perspective view of the distal end portion depicted in FIG. 9, as shown in a partially expanded configuration.
Figure 11:
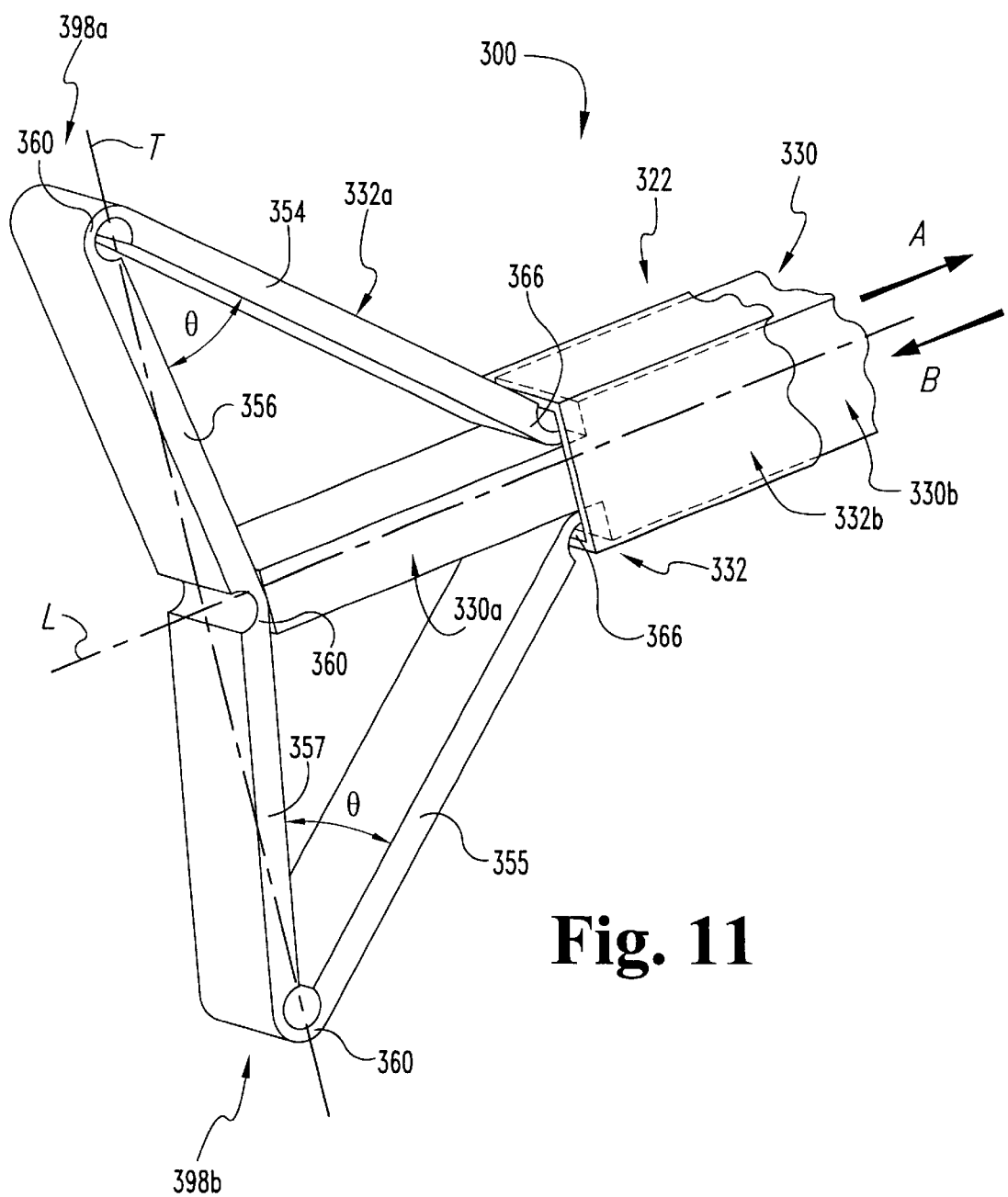
FIG. 11 is a perspective view of the distal end portion depicted in FIG. 9, as shown in a fully expanded configuration.

Referring now to FIGS. 9–11, shown therein is the distal end portion of an instrument 300 according to another form of the present invention, as shown in an initial insertion configuration, a partially deformed intermediate configuration, and a fully deformed configuration, respectively. It should be understood that instrument 300 may be used in association with applications similar to those discussed above with regard to instrument 20, including both intrabody and interbody applications involving displacement of at least a portion of a vertebral body.

Instrument 300 is comprised of an elongate member 322 extending generally along a longitudinal axis L and having a distal end portion (as shown) and a proximal end portion (not shown) which may be coupled to an actuator mechanism similar to actuator mechanism. The distal end portion is deformable and is configured to outwardly expand upon the imposition of a mechanically induced force. Specifically, the distal end portion is reformable between an initial configuration (FIG. 9) for positioning adjacent a vertebral body, and a deformed configuration (FIG. 11) for displacement of at least a portion of the vertebral body. Although the illustrated embodiment depicts elongate member 322 as having a generally linear, unitary configuration, it should be understood that elongate member 322 may take on other configurations as well, such as, for example, a curvilinear configuration or a hinged configuration.

In the illustrated embodiment of instrument 300, the elongate member 322 is generally comprised of an inner rod member 330 and an outer sleeve member 332. The inner rod 330 is preferably formed of a substantially rigid medical grade material such as, for example, titanium or stainless steel. Rod 330 includes a distal end portion 330a extending from a main body portion 330b. In the illustrated embodiment, the distal end portion 330a has a rectangular shape and the main body portion 330b has a square shape. However, it should be understood that other shapes and configurations of rod 330 are also contemplated as being within the scope of the present invention such as, for example, circular, elliptical or polygonal configurations.

The outer sleeve 332 has a deformable distal end portion 332a coupled to a main body portion 332b. The main body portion 332b has a square configuration defining an inner passage extending therethrough generally along longitudinal axis L and sized to slidably receive portion 330b of rod 330 therein. However, it should be understood that other shapes and configurations of sleeve portion 332b are also contemplated as being within the scope of the present invention. Preferably, the main body portion 332b is formed of a substantially rigid material, such as, for example, titanium, stainless steel or other substantially rigid medical grade materials.

The deformable distal end portion 332a of sleeve 332 is at least partially formed of a relatively flexible material that is capable of being reformed from the initial configuration illustrated in FIG. 9 toward the deformed configuration illustrated in FIG. 11. Preferably, distal end portion 332b is formed of a relatively elastic material that is capable of being elastically deformed toward the deformed configuration and reformed back toward the initial configuration. The deformable distal end portion 332b may be formed of materials including, but not limited to, titanium, stainless steel, an elastomer, a polymer, a rubber, a composite material or a shape-memory material. Distal end portion 332b is preferably formed separately from main body portion 332a and connected thereto by any method know to one of skill in the art, such as, for example, by fastening, welding or adhesion. However, is should be understood that distal end portion 332b could alternatively be formed integral with main body portion 332a to define a single-piece, unitary structure.

The deformable distal end portion 332a of sleeve 332 includes a plurality of wall elements 354–357 that are flexibly interconnected by a number or interconnection portions 360. In one embodiment of the invention, the interconnection portions 360 are defined by forming an opening or channel 362 at locations where adjacent wall elements adjoin to one another. In one embodiment of the invention, the wall elements 354–357 are integrally formed to define a unitary, single-piece reformable structure that is collapsible to define a relatively low-profile insertion configuration and expandable to define an outwardly deformed configuration.

To aid in reformation of the distal end portion 332a between the insertion and deformed configurations, the distal end portion 332a of sleeve 332 is preferably flexibly coupled to the main body portion 332b. In one embodiment, the outer wall elements 354, 355 each include a flexible interconnection portion 366 defined by forming an opening or channel 367 adjacent their respective distal end portions 354a, 355a. The distal end portions 354a, 355a of the outer wall elements 354, 355 are in turn coupled to inner surfaces of the main body portion 332b of sleeve 332, such as, for example, by fastening, welding or adhesion. The outer wall elements 354, 355 are separated by a distance sufficient to receive the distal end portion 330a of rod 330 therebetween.

As shown in FIG. 9, the insertion configuration has a substantially rectangular-shaped profile, with each of the wall elements 354–357 being disposed in a substantially uniform orientation (i.e., parallel to one another), and with the two inner wall elements 356, 357 being disposed between the two outer wall elements 354, 355. As shown in FIG. 11, the deformed/expanded configuration has a substantially triangular-shaped profile, with the two inner wall elements 356, 357 being disposed in a substantially parallel and co-linear orientation, and the two outer wall elements 354, 355 being disposed at an angle θ relative to inner wall elements 356, 357. In one embodiment, the angle θ is about 30°–45°. It should be understood that other insertion and expanded configurations are also contemplated as falling within the scope of the present invention. Additionally, although the reformable distal end portion 332b of sleeve 332 has been illustrated and described as including four wall elements 354–357, it should be understood that any number of wall elements may be flexibly interconnected to form the reformable distal end portion 332b.

When in the initial folded configuration illustrated in FIG. 9, the deformable distal end portion 332a of sleeve 332 has a relatively low profile to facilitate positioning adjacent a vertebral body. However, once properly positioned adjacent the vertebral body, the distal end portion 332a is mechanically deformed by displacing rod 330 relative to sleeve 332. In the illustrated embodiment, such relative displacement is accomplished by linearly displacing rod 330 relative to sleeve 332 in the direction of arrow B, and is initiated by the selective actuation of an actuator mechanism (not shown).

As shown in FIG. 10, relative displacement of rod 330 in the direction of arrow B causes the distal end portion 330a of rod 330 to engage the interconnection portion 360 extending between the inner wall elements 356, 357, thereby initiating the outward expansion or unfolding of the wall elements 354–357. In one embodiment of the invention, the distal end portion 330a of rod 330 is secured to the interconnection portion 360, such as, for example, by fastening, welding or adhesion. However, it should be understood that the distal end portion 330a of rod 330 need not necessarily be rigidly secured to interconnection portion 360, but could alternatively form an abutting relationship therewith to initiate the outward expansion of wall elements 354–357.

As shown in FIG. 11, when reformed to the deformed configuration, the wall elements 354–357 are unfolded and expanded outwardly relative to longitudinal axis L so as to form laterally extending projections or protrusions 398a, 398b disposed along a transverse axis T. Although instrument 300 has been illustrated and described as including a pair of oppositely disposed projections 398a, 398b when in the expanded configuration, it should be understood that the distal end portion 332a of sleeve 332 may be configured to define any number of projections, including a single projection or three or more projections. Further, similar to instrument 20, the expansion of the distal end portion 332a of sleeve 332 and the resulting displacement of the spinal structure accomplished by instrument 300 is directionally-controlled, and can be uniaxial, unidirectional or both uniaxial and unidirectional.

Following displacement of the vertebral body, the distal end portion 332a of sleeve 332 may be reformed toward its initial insertion configuration by linearly displacing rod 330 relative to sleeve 332 in the direction of arrow A (FIG. 11). As discussed above with regard to instrument 20, the distal end portion 332a of sleeve 332 may be formed of a shape-memory material, such as, for example, a shape-memory alloy ("SMA") to aid in reforming distal end portion 332a back toward its initial configuration.

Figure 12:
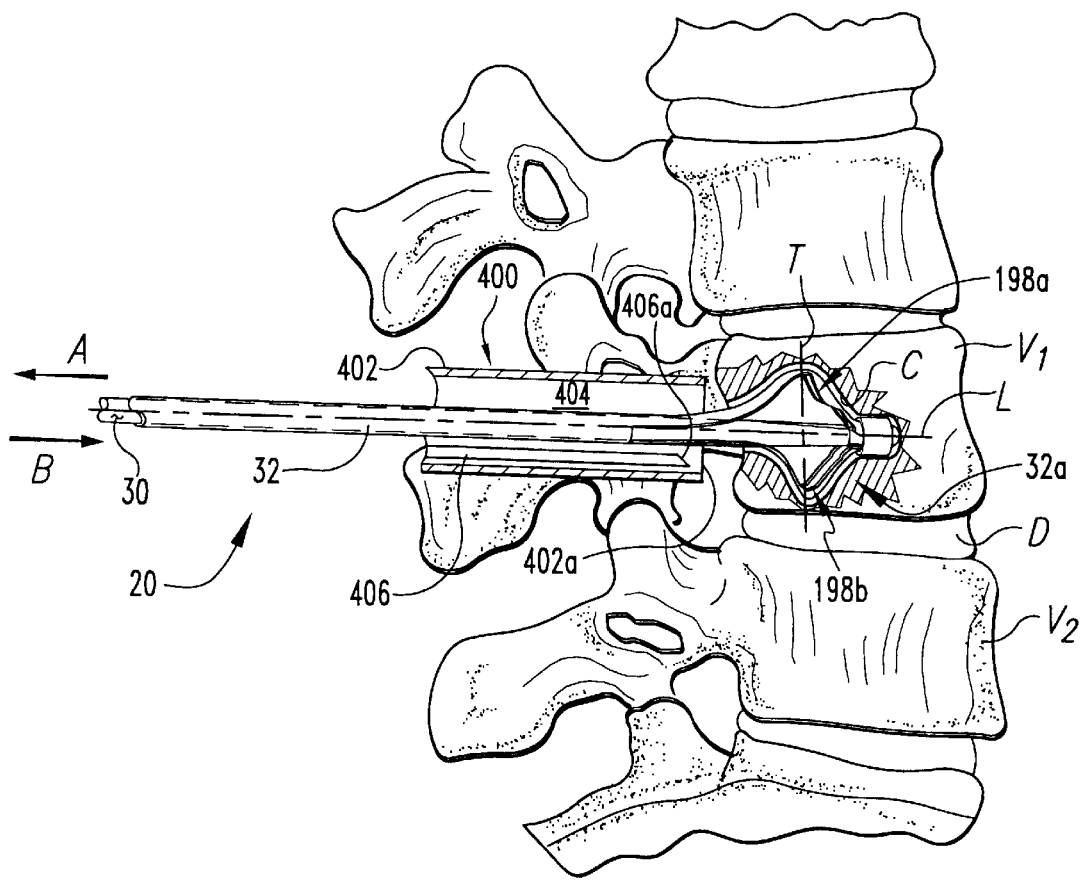
FIG. 12 is a partial cross-sectional side view of a spinal column illustrating treatment of a vertebral body using the surgical instrument illustrated in FIG. 1.

Referring to FIG. 12, shown therein is a lateral view of a spinal column, illustrating the introduction and expansion of instrument 20 within a vertebral body $V_1$ to perform intra-body distraction. The distal end portion 32a of sleeve 30 is initially passed through an access opening (not shown) extending through an outer wall of the vertebral body $V_1$ while in the undeformed initial configuration illustrated in FIG. 5. Subsequent to insertion within the vertebral body $V_1$, the distal end portion 32a of sleeve 32 is reformed by a mechanically-induced force created by linearly displacing rod 30 relative to sleeve 32 in the direction of arrow A. As a result, the distal end portion 32a is outwardly deformed to form opposing projections 198a, 198b extending along transverse axis T. Such outward deformation is particularly useful, for example, to compact or compress cancellous bone against the inner cortical wall of the vertebral body $V_1$ to form a cavity C therein. Compaction of the cancellous bone may have the effect of exerting an outward force on the inner surface of the cortical wall, making it possible to elevate or push broken and/or compressed bone back to or near its original pre-fracture condition or another desired condition. Alternatively, the opposing projections 198a, 198b may bear directly against the inner surface of the cortical bone to reduce a compression fracture in the vertebral body $V_1$.

In one form of the present invention, access into the inner cancellous region of the vertebral body $V_1$ is be accomplished by drilling a relatively small access opening through an outer wall of the vertebral body, such as, for example, through the pedicular region of the vertebral body $V_1$. The undeformed initial configuration of the distal end portion 32a of sleeve 30 is sized to pass through the small access opening to gain access to the inner cancellous region of the vertebral body $V_1$. In this manner, insertion of the distal end portion 32a of sleeve 32 is accomplished in a minimally invasive manner. Additionally, unlike certain prior art devices that require a relatively larger access opening to accommodate spreading of the proximal end portions of opposing members attached to one another in a scissors-like manner, only the distal end portion 32a of sleeve 32 is outwardly expanded when reformed toward the deformed configuration.

In one embodiment of the invention, the initial configuration of the distal end portion 32a of sleeve 32 is sized to pass through an access opening having a diameter between about 1 millimeter and about 5 millimeters. In a specific embodiment, the initial configuration of the distal end portion 32a is sized to pass through an access opening having a diameter of about 3 millimeters. In another embodiment of the invention, the deformed configuration of the distal end portion 32a of sleeve 30 is sized to displace the vertebral body $V_1$ within a range of about 3 millimeters to about 15 millimeters. In a specific embodiment, the deformed configuration of the distal end portion 32a is sized to displace the vertebral body $V_1$ about 10 millimeters. In another specific embodiment of the invention, the instrument 20 is capable of assuming a deformed configuration that is over three times greater than its initial configuration. Although ranges and specific sizes of the initial and deformed configurations of distal end potion 32b of sleeve 32 have been set forth above, it should be understood that such ranges and specific sizes are exemplary and are not intended to limit the scope of the present invention in any manner whatsoever.

Following displacement of the vertebral body $V_1$, the distal end portion 32a of sleeve 32 is reformed toward its initial insertion configuration by displacing rod 30 relative to sleeve 32 in the direction of arrow B. As a result, the opposing projections 198a, 198b are inwardly deformed to the extent necessary to provide uninhibited removal of the distal end portion 32a of sleeve 32 from the vertebral body $V_1$. As discussed above, reformation of the instrument 20 back toward its initial insertion configuration may be facilitated by forming the distal end portion 32a of sleeve 32 from a shape-memory material. Following the removal of instrument 20 from the vertebral body $V_1$, the cavity C may be filled with a biocompatible filling material, such as, for example, methylmethacrylate cement (e.g., bone cement), a structural implant, and/or a therapeutic substance to promote healing. Once set to a hardened condition, the filling material provides internal structural support to the vertebral body $V_1$, and more particularly provides structural support to the cortical bone of the vertebral body $V_1$.

In another form of the present invention, a cannula assembly 400 may be used to provide minimally invasive access to the vertebral bodies $V_1$, $V_2$ and/or the disc space D. As shown in FIG. 12, use of the cannula assembly 400 permits displacement of the vertebral body $V_1$ via insertion and manipulation of instrument 20 through a single working channel. Further details regarding a cannula assembly suitable for use in association with the present invention are disclosed in U.S. patent application Ser. No. 09/692,932 to Foley et al., filed on Oct. 20, 2000, the contents of which are incorporated herein by reference.

The cannula assembly 400 includes a cannula 402 having a distal end 402a and defining an inner working channel 404 extending between the distal end 402a and a proximal end (not shown). The length of the cannula 402 is sized such that the proximal end (not shown) of the cannula 402 is positioned beyond the skin of the patient when the distal end 402a is positioned adjacent the vertebral body $V_1$. One advantageous feature of the cannula assembly 400 is the relatively large cross section of the working channel 404 extending through cannula 402. Such a large cross section permits the surgeon to introduce a wide variety of instruments or tools into the working channel 404, as well as the simultaneous introduction of two or more instruments or tools. Furthermore, the relatively large cross section of working channel 404 permits a wide range of motion of the instruments and tools.

The cannula assembly 400 may also include an endoscope assembly (not shown) mounted to the proximal end portion of the cannula 402 to provide remote visualization of the surgical site. The endoscope assembly may include, for example, a viewing element 406 disposed within the working channel 404 of cannula 402 and having a distal end 406a positioned adjacent the surgical site. The viewing element 406 is preferably linearly and rotatably displaceable within the working channel 404 to provide a wide degree of visualization of the surgical site. The endoscope assembly may also include an illumination element (not shown), a remote viewing apparatus such as an eyepiece (not shown), and/or irrigation and aspiration components (not shown) extending along viewing element 406. One embodiment of an endoscope assembly suitable for use in association with the present invention is described in U.S. Pat. No. 6,152,871 to Foley et al., issued on Nov. 28, 2000, the contents of which are incorporated herein by reference. The cannula assembly 400 may also include a microscopic viewing system (not shown) mounted to the proximal end portion of the cannula 402 to provide microscopic visualization of the surgical site. One embodiment of a microscopic viewing system suitable for use in association with the present invention is described in U.S. patent application Ser. No. 09/815,693 to Foley et al., filed on Mar. 23, 2001, the contents of which are incorporated herein by reference.

Although FIG. 12 illustrates the use of instrument 20 to at least partially displace the vertebral body $V_1$, it should be understood that instruments 200 and 300 could alternatively be used to perform the technique. It should also be understood that in addition to performing intrabody distraction, instruments 20, 200 and 300 may be used to perform interbody distraction of one or both of the adjacent vertebral bodies $V_1$, $V_2$, such as, for example, to increase the height of the disc space D. Interbody distraction of adjacent vertebral bodies $V_1$, $V_2$ may also be effective to increase the distance between corresponding portions of the vertebral bodies $V_1$, $V_2$. In cases involving brittle portions of the vertebral bodies $V_1$, $V_2$, shims may be positioned between the deformable distal end portion 32a of sleeve 32 and the vertebral bodies $V_1$, $V_2$ to distribute the compressive force over a larger area to avoid puncturing or crushing of the brittle portions. It should additionally be understood that although the distraction technique illustrated in FIG. 12 uses a posterior surgical approach, other surgical approaches are also contemplated, such as, for example, anterior, lateral, and postero-lateral approaches.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. Instrumentation for treatment of the spine, comprising:
    an elongate member extending along a longitudinal axis and including a deformable distal end portion having an initial configuration for placement adjacent a spinal structure and a deformed configuration defining at least one transverse projection for transverse displacement of at least a portion of the spinal structure, each of said at least one transverse projection disposed along a single transverse axis such that said transverse displacement of the spinal structure is uniaxial.

2. The instrumentation of claim 1, wherein said transverse displacement of the spinal structure is directionally-controlled.

3. The instrumentation of claim 1, wherein said transverse displacement of the spinal structure is unidirectional.

4. The instrumentation of claim 1, wherein said deformed configuration defines a plurality of said transverse projections.

5. The instrumentation of claim 4, wherein said deformed configuration defines a pair of said transverse projections disposed generally opposite one another.

6. The instrumentation of claim 1, wherein said deformed configuration results from a mechanically induced force.

7. The instrumentation of claim 6, wherein said deformable distal end portion comprises a first member and a second member engaged with said first member; and
    wherein said second member is reformed from said initial configuration toward said deformed configuration by relative displacement between said first and second members.

8. The instrumentation of claim 7, wherein said relative displacement between said first member and said second member is relative linear displacement.

9. The instrumentation of claim 7, further comprising an actuator mechanism operably coupled to said first and second members to impart said relative displacement therebetween.

10. The instrumentation of claim 1, wherein said deformable distal end portion is at least partially formed of a relatively flexible material.

11. The instrumentation of claim 10, wherein said deformable distal end portion is at least partially formed of a relatively elastic material.

12. The instrumentation of claim 11, wherein said relatively elastic material is a shape-memory material.

13. The instrumentation of claim 11, wherein said deformable distal end portion is reformed from said initial configuration toward said deformed configuration in response to the imposition of stress, and is reformed toward said initial configuration upon removal of said stress.

14. The instrumentation of claim 1, wherein said transverse displacement comprises intrabody distraction of a vertebral body.

15. The instrumentation of claim 14, wherein said intrabody distraction comprises compaction of cancellous bone to form a cavity within the vertebral body.

16. The instrumentation of claim 14, wherein said intrabody distraction comprises at least partial reduction of a compression fracture in the vertebral body.

17. The instrumentation of claim 1, wherein said transverse displacement comprises interbody distraction of a vertebral body.

18. The instrumentation of claim 1, wherein said initial configuration is sized to pass through an access opening in the spinal structure having a diameter within a range of about 1 millimeter to about 5 millimeters; and
    wherein said deformed configuration is sized to transversely displace the spinal structure within a range of about 3 millimeters to about 15 millimeters.

19. Instrumentation for treatment of the spine, comprising:
    a first member;
    a second member having a distal end portion engaged with said first member, said distal end portion having an initial configuration for placement adjacent a spinal structure and an expanded configuration for displacement of at least a portion of the spinal structure; and
    wherein relative displacement between said first and second members causes said distal end portion to reform from said initial configuration toward said expanded configuration, said expanded configuration defining at least one transverse projection, each of said at least one transverse projection disposed along a single transverse axis such that said displacement of the spinal structure is uniaxial.

20. The instrumentation of claim 19, further comprising an actuator mechanism coupled between said first and second members and being operable to impart said relative displacement therebetween.

21. The instrumentation of claim 20, wherein said actuator mechanism is operable to reform said distal end portion of said second member from said expanded configuration back toward said initial configuration.

22. The instrumentation of claim 20, wherein said actuator mechanism comprises:
  a first portion coupled to said first member; and
  a second portion coupled to said second member and engaged with said first portion; and
  wherein relative rotation between said first and second portions imparts relative linear displacement between said first and second members to cause said distal end portion to reform from said initial configuration toward said expanded configuration.

23. The instrumentation of claim 22, wherein said first portion of said actuator mechanism comprises a T-handle.

24. The instrumentation of claim 19, wherein said distal end portion of said second member is at least partially formed of a relatively elastic material to facilitate reformation from said initial configuration to said expanded configuration and back toward said initial configuration.

25. The instrumentation of claim 19, wherein said at least one transverse projection comprises an outward deformation.

26. The instrumentation of claim 25, wherein said distal end portion of said second member includes a pair of said outward deformations positioned generally opposite one another when in said expanded configuration.

27. The instrumentation of claim 19, wherein said distal end portion of said second member comprises at least one flexible strip of material, said flexible strip of material buckling outwardly in response to said relative displacement between said first and second members to form said at least one transverse projection.

28. The instrumentation of claim 27, wherein outward buckling of said flexible strip of material occurs in a predetermined direction.

29. The instrumentation of claim 27, wherein said distal end portion of said second member comprises a pair of said flexible strips of material disposed generally opposite one another, said flexible strips of material buckling outwardly in response to said relative displacement between said first and second members to form a pair of said at least one transverse projections disposed generally opposite one another.

30. The instrumentation of claim 27, wherein said flexible strip of material has a predetermined shape to provide controlled outward buckling.

31. The instrumentation of claim 19, wherein said distal end portion of said second member defines a plurality of slots, said slots facilitating outward buckling of said distal end portion in response to said relative displacement between said first and second members.

32. The instrumentation of claim 31, wherein each of said plurality of slots has a predetermined shape to provide controlled outward buckling.

33. The instrumentation of claim 19, wherein said distal end portion of said second member comprises a plurality of elements flexibly interconnected in series to form a reformable structure, said reformable structure being collapsible to define said initial configuration and expandable to define said expanded configuration.

34. The instrumentation of claim 33, wherein said plurality of elements are elastically interconnected.

35. The instrumentation of claim 33, wherein said distal end portion has a substantially rectangular-shaped profile when in said initial configuration and a substantially triangular-shaped profile when in said expanded configuration.

36. The instrumentation of claim 33, wherein said plurality of elements are disposed in a substantially uniform orientation when in said initial configuration, and wherein at least some of said plurality of elements are disposed in a non-uniform orientation when in said expanded configuration.

37. The instrumentation of claim 33, wherein said plurality of elements are integrally formed to define a single-piece reformable structure.

38. The instrumentation of claim 33, wherein said second member includes a sleeve portion, said plurality of elements being coupled to said sleeve portion; and
  wherein said second member is displaceable through said sleeve portion and engages at least one of said plurality of elements to transition said plurality of elements between said initial configuration and said expanded configuration.

39. The instrumentation of claim 33, wherein an adjacent pair of said plurality of elements cooperates to define a laterally extending protrusion when in said expanded configuration.

40. The instrumentation of claim 19, wherein reformation between said initial configuration and said expanded configuration is directionally-controlled.

41. Instrumentation for treatment of the spine, comprising:
  a first member;
  a second member having a distal end portion engaged with said first member, said distal end portion having an initial configuration for placement adjacent a spinal structure and an expanded configuration for displacement of at least a portion of the spinal structure; and
  wherein relative displacement between said first and second members causes said distal end portion to reform from said initial configuration toward said expanded configuration; and
  wherein said distal end portion of said second member comprises at least one flexible strip of material, said flexible strip of material buckling outwardly in response to said relative displacement between said first and second members to form said expanded configuration, said flexible strip of material having a predetermined shape to provide controlled outward buckling, said predetermined shape including a series of arcuate portions.

42. Instrumentation for treatment of the spine, comprising:
  a first member;
  a second member having a distal end portion engaged with said first member, said distal end portion having an initial configuration for placement adjacent a spinal structure and an expanded configuration for displacement of at least a portion of the spinal structure; and
  wherein relative displacement between said first and second members causes said distal end portion to reform from said initial configuration toward said expanded configuration; and wherein said distal end portion of said second member defines a plurality of slots, said slots facilitating outward buckling of said distal end portion in response to said relative displacement between said first and second members, each of said plurality of slots has a predetermined shape to provide controlled outward buckling, said predetermined shape being at least partially comprised of an hour-glass shape.

43. Instrumentation for treatment of the spine, comprising:

a member including a deformable distal end portion having an initial configuration for positioning adjacent a spinal structure and a deformed configuration for displacing the spinal structure; and means for mechanically deforming said distal end portion from said initial configuration toward said deformed configuration to displace at least a portion of the spinal structure in at least one predetermined direction.

44. A method for treatment of the spine, comprising:

providing an instrument including a distal end portion, the distal end portion having an insertion configuration and a deformed configuration;

positioning the distal end portion adjacent a spinal structure while in the insertion configuration; and deforming the distal end portion toward the deformed configuration to displace at least a portion of the spinal structure, wherein the deforming is directionally controlled.

45. The method of claim 44, further comprising:

deforming the distal end portion back toward the insertion configuration; and removing the distal end portion from the spinal structure.

46. The method of claim 44, wherein the deforming occurs in response to the imposition of a mechanically induced force.

47. A method for treatment of the spine, comprising:

providing an instrument including a distal end portion, the distal end portion having an insertion configuration and a deformed configuration and comprising a first member and a second member engaged with the first member; and positioning the distal end portion adjacent a spinal structure while in the insertion configuration; and deforming the distal end portion toward the deformed configuration to displace at least a portion of the spinal structure, wherein the deforming occurs in response to relative displacement between the first member and the second member to outwardly deform at least a portion of the second member to form at least one laterally extending projection.

48. The method of claim 47, wherein the relative displacement comprises linear displacement of the first member relative to the second member.

49. The method of claim 44, wherein the positioning comprises inserting the distal end portion through an outer wall of a vertebral body; and wherein displacement of the at least a portion of the spinal structure comprises compacting bone to a cavity within the vertebral body.

50. The method of claim 44, further comprising:

inserting a cannula having a working channel through the skin and tissue of a patient;

positioning a distal end of the cannula adjacent the vertebral body; and inserting the distal end portion of the instrument through the working channel to access the vertebral body.

51. The method of claim 50, further comprising:

inserting a viewing element into the working channel of the cannula to provide visualization of the vertebral body.

* * * * *